United States Patent
Jeong et al.

(10) Patent No.: US 10,464,037 B2
(45) Date of Patent: Nov. 5, 2019

(54) METHOD FOR ENCAPSULATING A NANOSTRUCTURE, COATED NANOSTRUCTURE AND USE OF A COATED NANOSTRUCTURE

(71) Applicant: MAX-PLANCK-GESELLSCHAFT ZUR FÖRDERUNG DER WISSENSCHAFTEN E.V., München (DE)

(72) Inventors: Hyeon-Ho Jeong, Stuttgart (DE); Tung Chun Lee, Hong Kong (CN); Peer Fischer, Freiburg (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 0 days.

(21) Appl. No.: 15/562,221

(22) PCT Filed: Mar. 23, 2016

(86) PCT No.: PCT/EP2016/056377
§ 371 (c)(1),
(2) Date: Sep. 27, 2017

(87) PCT Pub. No.: WO2016/156148
PCT Pub. Date: Oct. 6, 2016

(65) Prior Publication Data
US 2018/0117560 A1 May 3, 2018

(30) Foreign Application Priority Data

Mar. 27, 2015 (EP) .................... 15161329

(51) Int. Cl.
| | |
|---|---|
| *C23C 14/04* | (2006.01) |
| *C23C 16/04* | (2006.01) |
| *C23C 28/00* | (2006.01) |
| *B01J 13/04* | (2006.01) |
| *B01J 13/02* | (2006.01) |
| *C23C 14/22* | (2006.01) |
| *C23C 16/44* | (2006.01) |
| *A61K 9/50* | (2006.01) |
| *H01M 10/0525* | (2010.01) |
| *B82Y 40/00* | (2011.01) |
| *B82Y 30/00* | (2011.01) |
| *C23C 18/08* | (2006.01) |
| *C23C 18/14* | (2006.01) |
| *H01G 9/20* | (2006.01) |

(52) U.S. Cl.
CPC ............. *B01J 13/04* (2013.01); *A61K 9/5089* (2013.01); *B01J 13/02* (2013.01); *C23C 14/04* (2013.01); *C23C 14/042* (2013.01); *C23C 14/226* (2013.01); *C23C 16/04* (2013.01); *C23C 16/042* (2013.01); *C23C 16/4417* (2013.01); *H01M 10/0525* (2013.01); *B82Y 30/00* (2013.01); *B82Y 40/00* (2013.01); *C23C 18/08* (2013.01); *C23C 18/14* (2013.01); *H01G 9/2059* (2013.01)

(58) Field of Classification Search
CPC ....... C23C 14/04; C23C 14/226; C23C 16/04; C23C 28/00
See application file for complete search history.

(56) References Cited

U.S. PATENT DOCUMENTS

| | | | |
|---|---|---|---|
| 6,206,065 B1 | 3/2001 | Robbie et al. | |
| 6,479,146 B1 | 11/2002 | Caruso et al. | |
| 8,017,181 B2 | 9/2011 | Shin et al. | |
| 8,735,174 B2 | 5/2014 | Mirkin et al. | |
| 8,768,501 B2 | 7/2014 | Fischer et al. | |
| 8,802,441 B2 | 8/2014 | Khan et al. | |
| 2008/0057260 A1* | 3/2008 | Buchhauser | H01L 51/524 428/76 |
| 2010/0310784 A1 | 12/2010 | Knapp et al. | |
| 2014/0127305 A1 | 5/2014 | Ortac et al. | |
| 2015/0167146 A1* | 6/2015 | McMurtry | B01J 13/043 206/524.3 |

FOREIGN PATENT DOCUMENTS

| | | |
|---|---|---|
| CN | 102370995 A | 3/2012 |
| DE | 102007017032 B4 | 9/2011 |
| WO | 2007143076 A2 | 12/2007 |
| WO | 2013186292 A2 | 12/2013 |
| WO | 2015025314 A1 | 2/2015 |

(Continued)

OTHER PUBLICATIONS

Amar B. Pawar et al., Patchy Particles by Glansing Angle Deposition, Langmuir, 2008, pp. 355-358, vol. 24, No. 2, American Chemical Society.
Andrew G. Mark et al., Hybrid nanocolloids with programmed three-dimensional shape and material composition, Nature Materials, Jun. 23, 2013, pp. 802-807, vol. 12, Macmillan Publishers Limited, Stuttgart, Germany.
Christina Graf et al., A General Method to Coat Colloidal Particles with Silica, Langmuir, 2003, pp. 6693-6700, vol. 19, No. 17, American Chemical Society.

(Continued)

*Primary Examiner* — Jake M Vu
*Assistant Examiner* — Jagadishwar R Samala (57) ABSTRACT

The present invention relates to a method for encapsulating a nanostructure, the method comprising the steps of:
providing a substrate;
forming a plug composed of plug material at said substrate;
forming a nanostructure (on or) at said plug;
forming a shell composed of at least one shell material on external surfaces of the nanostructure, with the at least one shell material covering said nanostructure and at least some of the plug material, whereby the shell and the plug encapsulate the nanostructure. The invention further relates to a coated nanostructure and to the use of a coated nanostructure.

17 Claims, 7 Drawing Sheets

(56) References Cited

FOREIGN PATENT DOCUMENTS

WO 2015042204 A1 3/2015
WO 2015192149 A2 12/2015

OTHER PUBLICATIONS

Chuanbo Gao et al., Highly Stable Silver Nanoplates for Surface Plasmon Resonance Biosensing**, Angewandte Chemie International Edition, 2012, pp. 5629-5633, vol. 51, Wiley-VCH Verlag GmbH and Co. KGaA, Weinheim, Germany.

Chunyuan Song et al., Ag—SiO2 Core-Shell Nanorod Arrays: Morphological, Optical, SERS, and Wetting Properties, Langmuir, 2012, pp. 1488-1495, vol. 28, American Chemical Society.

International Preliminary Report on Patentability for International Application No. PCT/EP2016/056377, dated Oct. 3, 2017, 11 pages.

International Search Report for International Application No. PCT/EP2016/056377 dated May 27, 2016, 3 pages.

J. Li et al., Shell-Isolated nanoparticle-enhanced Raman spectroscopy, Nature 2010, Abstract only, 1 page.

Jian Feng et al., Surface analysis using shell-isolated nanoparticle enhanced Raman spectroscopy, Nature Protocols, 2013, pp. 52-65, vol. 8, No. 1, Nature America, Inc.

Philipp Reineck et al., Distance and Wavelength Dependent Quenching of Molecular Fluorescence by Au@SiO2 Core-Shell Nanoparticles, ACS Nano, 2013, pp. 6636-6648, vol. 7, No. 8, American Chemical Society.

Supratim Giri et al., Stimuli-Responsive Controlled-Released Delivery System Based on Mesoporous Silica Nanorods Capped with Magnetic Nanoparticles, Angewandte Chemie International Edition, 2005, pp. 5038-5044, Wiley-VCH Verlag GmbH and Co. KGaA, Weinheim, Germany.

Wei Wang et al., Ag@SiO2 Core-Shell Nanoparticles for Probing Spatial Distribution of Electromagnetic Field Enhancement via Surface-Enhanced Raman Scattering, ACS Nano, 2009, pp. 3493-3496, vol. 3, No. 11, American Chemical Society Written Opinion for International Application No. PCT/EP2016/056377 dated Oct. 6, 2016, 10 pages.

X H Yang et al., Hybrid Ag@TiO2 core-shell nanostructures with highly enhanced pnotocatalytic performance, Nanotechnology, pp. 1-10, IOP Publishing Ltd.

Zhaosheng Hu et al., Wafer-Scale Double-Layer Stacked Au/Al2O3 @Au Nanosphere Structure with Turnable Nanospacing for Surface-Enhanced Raman Scattering, small, 2014, pp. 3933-3942, vol. 10, No. 19, Wiley-VCH Verlag GmbH and Co. KGaA, Weinheim, Germany.

European Examination Report for European Application No. 16711632.6 dated Feb. 8, 2019, 10 pages.

Hyeon-Ho Jeong et al., "Shape control in wafer-based aperiodic 3D nanostructures," Nanotechnology, May 21, 2014, vol. 25,IOP Publishing, United Kingdom, 7 pages.

* cited by examiner

METHOD FOR ENCAPSULATING A NANOSTRUCTURE, COATED NANOSTRUCTURE AND USE OF A COATED NANOSTRUCTURE

CROSS-REFERENCES TO RELATED APPLICATIONS

This patent application is a 371 of International Application No. PCT/EP2016/056377, filed Mar. 23, 2016 which claims the priority of European Application No. 15161329.6, filed Mar. 27, 2015 each of which are incorporated herein by reference in their entirety.

The present invention relates to a method for encapsulating a nanostructure, to a coated nanostructure and to a use of a coated nanostructure.

In the production of nanostructures several kinds of materials are of interest. For example, pure and alloyed colloidal particles of metallic, magnetic, semiconducting, dielectric, and meta-materials are of immense interest due to their potential unique electronic, optical, magnetic, and catalytic properties. Moreover, pharmaceutical materials are of interest in order to e.g. reduce the dosage of medication administered to a patient. Unfortunately a wide variety of these materials are not only difficult to fabricate, but are also unstable in solution (due to corrosion, dissolution, oxidation etc.), or are toxic. This means that some materials cannot be produced easily and other materials cannot be handled once produced, so that only well-known stable materials such as gold (Au), and some oxides are used in various applications to date. For this reason solution-based applications and applications in biological media of nanoparticles made from materials that may have special electric, magnetic and/or optical effects are currently not able to be realised in a stable form.

It is known in the art to protect a material using so-called wet chemistry. For example a silica ($SiO_2$) shell can be produced to surround a core material/structure. However, this method has the following critical limitations: first of all, solution-based protection techniques limit the possible core materials that can be used in the first place as the core material may oxidise and corrode before it is properly protected by the shell. Secondly, the method needs careful optimization whenever the core material is changed. A further difficulty that has to be overcome is that, if the shell must be of high quality and of a well-defined thickness, then the reproducibility of such structures is still challenging at the nanoscale. Thirdly, a wet chemical protection method is restricted to a few materials as many materials dissolve or degrade in the presence of the solutions used.

In contrast to this, physical methods including sputtering and other forms of deposition, such as pulsed laser deposition, atomic layer deposition ALD, physical vapour deposition (PVD), glancing angle deposition (GLAD), molecular beam epitaxy (MBE), and chemical vapour deposition (CVD) can for instance be used to grow a nanoshell on top of a target particle as a protection layer. The desired reproducibility can be achieved using such physical methods, as these permit the growth of highly uniform surfaces with the full flexibility over a large choice of materials and their shapes at an atomic scale resolution.

However, physical methods have one critical drawback for the protection of the particle (core material). They generally cannot ensure a complete coverage of the nanostructure so that the nanostructure is not fully encased and thus the core is not completely protected. Thus, when the coated particle is transferred to a solution, to a reactive gaseous environment, or to a biological medium, this causes corrosion of the particle core, or a leakage of e.g. toxic core material, or the degradation of the core material over time.

For this reason it is a principal object of the present invention to provide a completely encapsulated nanostructure. It is a further object of the invention to produce a coated nanostructure that can be fabricated in a reproducible and uniform manner. It is yet a further object of the invention to make available a method of fabricating coated nanostructures for a wider range of materials than was previously possible.

This object is satisfied by a method in accordance with claim 1. Thus, the method in accordance with the invention for encapsulating a nanostructure comprises the steps of:
providing a substrate;
forming a plug composed of plug material at said substrate;
forming a nanostructure on or at said plug;
forming a shell composed of at least one shell material on external surfaces of the nanostructure, with the at least one shell material covering said nanostructure and or binding to at least some of the plug material, whereby the shell and the plug in combination preferably completely encapsulate the nanostructure.

The method is preferably carried out in a gaseous and/or vacuum atmosphere, with the vacuum atmosphere being selected to permit the formation of at least the shell, and the plug. This advantageously permits e.g. the use of a PVD or CVD process to control the formation rates of the plug or shell and enables these to be fabricated in a reproducible manner. Moreover, the use of a gaseous and/or vacuum atmosphere also avoids the use of solvents that may dissolve or deteriorate the core material.

In this way the particles of the core material that are deposited on a substrate, are fully protected when separated from the substrate even though the "substrate-side" of the particles is generally not protected by a coating, but rather, in accordance with the invention, due the presence of the plug. Thus when the coated particle is transferred to solution, to a reactive gaseous environment, or to a biological medium, the sealed particle core is protected from corrosion, from leakage of e.g. toxic core material, and from unwanted or premature degradation of the core material.

Thus, the invention makes available a method for the fabrication and application of stable nanoparticles and nanocolloids. Core-shell particles in the size range from a few nanometers up to several microns in one spatial dimension can be fabricated using such a method, for example, the nanostructure can be formed at said plug having a size selected in the range of 10 nm to 10000 nm in at least one dimension thereof. The core of the encapsulated nanostructure, i.e. the nanostructure itself or a functionalized or coated nanostructure, is or can include a material of interest that should e.g. be protected by means of the shell or functionalized by way of the shell. The core of the encapsulated nanostructure can contain a functional material and can be fabricated using metals, magnetic materials, insulators, and semiconductors, or any other material that can be suitably deposited or grown as a nanostructure on top of a seed, and/or combinations thereof.

Crucial is a "plug" that is formed as an insoluble, stable partition layer between the supporting substrate, and as a protection layer at the substrate side of the core. The plug can also potentially provide electrical insulation and prevent dissolution and corrosion of the core material, alternatively the plug can prevent toxic materials from leaking out of the encapsulated nanostructure into the environment. Thus, the shell, together with the plug, forms an intact protection layer that can completely isolate the remaining core part from the outside environment to prevent, corrosion, dissolution, to electrically insulate the particle, and to prevent toxic materials to leak into the environment. Both the plug and the shell material can also serve as a diffusion barrier to gases or molecules.

It is preferred if the plug is adapted to act as a physical and/or chemical barrier from the substrate and/or the environment, in particular by selecting a material, such as a polymer or an oxide or a metal, as the material of the plug.

It is also beneficial if the shell is adapted to act as a physical and/or chemical barrier from the substrate and/or the environment, in particular by selecting a material, such as a polymer or an oxide or a metal, as the material of the shell. In this connection it should be noted that if the plug and the shell are selected to together form a physical and/or chemical barrier from the substrate and the environment, i.e. to together form an intact coating, then the fully encapsulated core—can be protected from corrosion or dissolution of the core material. Thereby the core material can be shielded from the environment when gases or liquids or external potential(s) (e.g. electric, chemical, and phoretic) are present.

Employing such a method of manufacture permits the growth of custom tailored nanoparticles that are, for instance, magnetic and that can be used in targeting cells. The shell permits chemical functionalization and the core structure can give the nanoparticle functions that cannot or only with difficulty be realized with other methods of manufacture. The method described herein makes it possible to grow nanostructures that contain multiple functionalities and that are stable in solution, for example for the use as or in:

Contrast agents for imaging (MRI)
Magnetic materials for hyperthermia treatment
Nano- and micropropeller shapes for movement and drug delivery
Particles with magnetic materials for magnetic therapy
Particles with magnetic materials for rheological applications
Anisotropic magnetic particles for magnetic therapy
Radioactive materials
Plasmonic activity
Use of materials that cannot be used to make nanoparticles by conventional means and to protect these materials.

Preferably, the plug material is adapted to act as an impenetrable barrier from the substrate, in particular by selecting an electrical insulator material, such as PTFE or SiO2, as the material of the plug.

Preferably in the region in which the shell covers at least some of the plug material the shell is connected to the plug material, for example by means of a chemical bond, a physical bond (e.g. due to inter-engaging surface roughness), or van der Waals forces.

Advantageously the plug is formed by a sputtering or other deposition process, such as a pulsed laser deposition process, a physical vapour deposition (PVD) process, a chemical vapour deposition (CVD) process, an atomic layer deposition (ALD) process, a glancing angle deposition (GLAD) process, molecular beam epitaxy (MBE), by electro- or electroless deposition, or by a printing or nanoimprinting method. These processes advantageously permit a uniform and reproducible formation of the plug.

Preferably the plug is formed to have a predefinable size and shape, with the pre-definable size and shape of the plug optionally being selected at least substantially in conformity with at least one size and/or shape of the nanostructure.

Advantageously the shell is formed by a sputtering or other deposition process, such as a pulsed laser deposition process, a physical vapour deposition (PVD) process, a chemical vapour deposition (CVD) process, an atomic layer deposition (ALD) process, a glancing angle deposition (GLAD) process, molecular beam epitaxy (MBE), by electro- or electroless deposition, or by a printing or nanoimprinting method These processes advantageously permit a uniform and reproducible formation of the shell.

It is preferred when a material of the plug is selected from the group of materials comprising: oxides, such as $SiO_2$, $Al_2O_3$, $TiO_2$, $Ta_2O_5$, $HfO_2$, inert stable materials including metals, such as Pt, Au or Ti, or metal alloys. These materials can be produced in a cost effective way, provide the plug with its essential functions and enable a complete encasing of the nanostructure.

It is also preferred if a material of the shell is selected from the group of materials comprising: oxides, such as $SiO_2$, $Al_2O_3$, $TiO_2$, $Ta_2O_5$, $HfO_2$, inert stable materials including metals, such as Pt, Au or Ti, or their alloys. These materials can be produced in a cost effective way, provide the shell with its essential functions and, with the plug, enable a complete encasing of the nanostructure.

In some instances it may be advantageous if the shell is formed from the same material as the plug. In this way the same method of forming the plug and the shell can be employed and the same setup can be used reducing the cost of manufacture of encapsulated nanostructures.

Preferably the nanostructure is composed of at least one core material, and in the case of plural materials with these different materials either being mixed or arranged adjacent to one another. In this way the design of the nanostructure can be tailored to its specific use.

Advantageously the nanostructure is formed by a growth technique selected from the group comprising physical vapour deposition (PVD), chemical vapour deposition (CVD), electro- or electroless deposition, molecular beam epitaxy and inkjet printing. These processes advantageously permit a uniform and reproducible formation of the nanostructure.

It is preferred if a material of the nanostructure is selected from the group of materials comprising: Ag, Au, Cu, Al, Co, Ni, Fe, Gd, Pt alloys, oxides and combinations of the aforementioned materials, in particular $Fe_2O_3$ and $Fe_3O_4$, a compound of a contrast agent for imaging, a compound of magnetic material for hyperthermia treatment, a compound of material for nano- and miccropropeller shapes for movement and drug delivery, a compound of material having magnetic properties for magnetic therapy and rheology, radioactive materials, materials exhibiting plasmonic activity, materials susceptible to oxidation. In this connection it should be noted that a material of the nanostructure could also be selected from the following materials: Mg, Ca, Na and Li.

These materials can partly be produced in a cost effective way, provide the nanostructure with its essential function and enable an application specific targeting of the nanostructure.

In some instances it is advantageous if a layer of plug binding material is deposited between the plug and the core material in order to ensure that the core material adheres to the plug. The layer of plug binding material may comprise Ti, or Cr.

Likewise it is also possible to deposit a layer of shell binding material on the core prior to depositing the shell on the core. The layer of shell binding material may comprise Ti, or Cr.

In some instances the layer of plug binding material may be the same as the layer of shell binding material. In particular in those instances where the plug and the shell are formed from the same material.

Advantageously the method comprises the further step of separating the encapsulated nanostructure from the substrate to form a discrete encapsulated nanostructure.

Using mechanical agitations, such as e.g. by sonication, the encapsulated nanostructures can be separated from the substrate and subsequently utilized for their intended use.

Advantageously the method comprises the further step of providing a sacrificial layer on the substrate prior to the step of forming the plug. Such a sacrificial layer can advantageously be used to subsequently facilitate the separation of the encapsulated nanostructures from the substrate.

Preferably the method comprises the further step of providing seeds on the substrate prior to or directly after the step of providing a plug, with the seeds being provided in a patterned manner on said substrate or on the plug material. Using seeds on or impurities at a surface of the substrate advantageously permits the seeds or impurities to act as a growth promoter for the nanostructures. The seeds can for example be selected from the group of materials including: Au, Pt, Ag, $Fe_2O_3$ and $Fe_3O_4$, $SiO_2$ etc.

In a further use of the method the step of forming the plug and/or the step of providing the nanostructure is effected by a lithographic technique, such as photo-lithography, e-beam lithography, two photon lithography, or nano-imprint lithography. In this way the shape and size of both the plug and the nanostructure can be predefined by the mask that is employed during the lithographic technique. Such a technique advantageously permits coated nanostructures to be grown that have a high level of uniformity and that can be reproduced in a desirable way.

The plug material may, however, also be chosen to decompose or disintegrate in an environment of use when gases or liquids are present in the environment. This is advantageous if the core material should dissolve in a region of interest that may for instance be characterized by a different chemical environment.

Advantageously the plug and the nanostructure can then be removed to form a hollow shell. In this case the method permits the growth of nanostructured shells.

For some applications it is advantageous if the shell is composed of a plurality of different materials or shell layers of different material. In this way more degrees of freedom exist in the way the shell can be formed.

Preferably the shell is deposited in the form of at least one layer of a biologically active or pharmaceutical material and at least one further layer encapsulating the at least one layer of biologically active or pharmaceutical material.

This is advantageous for example in those cases where the nanostructure is a nano-propeller, as then e.g. the pharmaceutical material can be transported in the human body to its target position and the further layer encapsulating the at least one layer of biologically active or pharmaceutical material and/or the plug can be selected to decompose within a predefined time period, so that the biologically active or pharmaceutical material can be delivered at the target position in a metered manner, reducing the overall dose administered to a patient.

In a further aspect the invention relates to a coated nanostructure. The coated nanostructure, comprises:
a nanostructure;
a shell covering said nanostructure except at least one position; and
a plug at the or each at least one position, the shell and the plug encapsulating the nanostructure.

The nanostructure in accordance with the invention can be further developed in a similar manner to and shows similar advantages to the method. Such advantageous features are described in an exemplary, but not exclusive manner in the subordinate claims dependent on the independent claims.

Advantageously the shell of the coated nanostructure is composed of a plurality of different materials or shell layers of different materials.

In this connection it should be noted that the shell could also be composed of a layer of material formed naturally on the material of the core. This means that the shell is formed from e.g. a natural oxide and does not necessarily need to be deposited as a layer of shell material.

Preferably the shell comprises at least one inner layer of a biologically active or pharmaceutical material and at least one further layer encapsulating the at least one inner layer of biologically active or pharmaceutical material.

In some cases it is preferred when the shell is selected to be dissolved or disintegrated by or in the presence of a body fluid, and/or by an environmental chemical.

Advantageously the plug of the coated nanostructure is selected to be dissolved or disintegrated by or in the presence of a body fluid, and/or by an environmental chemical.

Advantageously the nanostructure is selected from the group comprising Ag, Au, Cu, Al, Co, Ni, Fe, Gd, Pt, Mg, Ca, Na, Li alloys, oxides and combinations of the aforementioned materials, in particular $Fe_2O_3$ and $Fe_3O_4$, a compound of a contrast agent for imaging, a compound of magnetic material for hyperthermia treatment, a compound of material for formation of nanopropeller shapes for movement and drug delivery, materials having magnetic moments for magnetic therapy, including paramagnetic, superparamagnetic and ferromagnetic ones, a compound of material for formation of a anisotropic rod-like shape to experience a torque in a magnetic field for magnetic therapy, radioactive materials, materials exhibiting plasmonic activity, materials susceptible to oxidation.

In a further aspect the present invention relates to a use of a coated nanostructure produced in accordance with the method of the invention and/or in accordance with the coated nanostructure in accordance with the invention, as a compound of a contrast agent for imaging, such as plug=$Al_2O_3$, core=Gd, shell=$Al_2O_3$, a compound of a magnetic material for hyperthermia treatment, such as plug=$Al_2O_3$, core=$Fe_2O_3$, shell=$Al_2O_3$, a compound of material for the formation of nanopropeller shapes for movement and drug delivery, such as plug=$Al_2O_3$, core=Ni and $SiO_2$, shell=$SiO_2$, a compound of material for the thermal treatment of diseased or abnormal tissue, a compound of material having magnetic properties for magnetic therapy, such as plug=$Al_2O_3$, core=Co, shell=$SiO_2$, radioactive materials, materials exhibiting plasmonic activity, such as plug=$SiO_2$, core=Ag or Au, shell=$SiO_2$, protection of materials that degrade without a coating, such as by oxidation, or in the presence of environmental fluids, e.g. Ag, Co, etc.

In a preferred use of a coated nanostructure produced in accordance with the method of the invention this is used as a compound of material having magnetic properties for magnetic therapy, with the nanostructure having a plug formed of Ti, a core formed of Co and a shell formed of $HfO_2$.

The invention will be explained in more detail in the following also with respect to further features and advantages by way of example with reference to embodiments and to the enclosed drawing. The Figures of the drawing show in:

FIG. 1a-e a first scheme detailing the fabrication process of encapsulated nanostructures, FIG. 2a-b a) a TEM image of a fabricated encapsulated nanostructure, b) EDX mapping images of the encapsulated nanostructure of FIG. 2a, FIG. 3 comparisons of the lifetime of a coated nanostructure, a coated nanostructure without a plug and a nanostructure without a coating in the presences of a) 1 mM $H_2O_2$ and b) acetate buffer pH4-6.

FIG. 1 shows a first scheme detailing the fabrication process of encapsulated nanostructures 10. In a first step of the fabrication of stable colloidal core-shell particles 10, an array of seeds 12 is provided at a substrate 14. The array of seeds 12 can be provided in a predefined pattern (see FIG. 1a). Following the provision of the seeds 12 a respective plug 16 is formed on the seeds 12 (see FIG. 1b). Thereafter a nanostructure 18 is formed on the plug (see FIG. 1c). The nanostructure 18 forms a core of the core-shell particle 10. The next step in the sequence for the fabrication of stable colloidal core-shell particles 10 is the formation of a shell 20 on the nanostructure 18 (see FIG. 1d). The final step shown in FIG. 1 is that depicted in FIG. 1e, where the core-shell particles 10 are present in a colloidal solution of core-shell particles 10 following the detachment of the core-shell particles 10 from the substrate 14.

Figure 1:
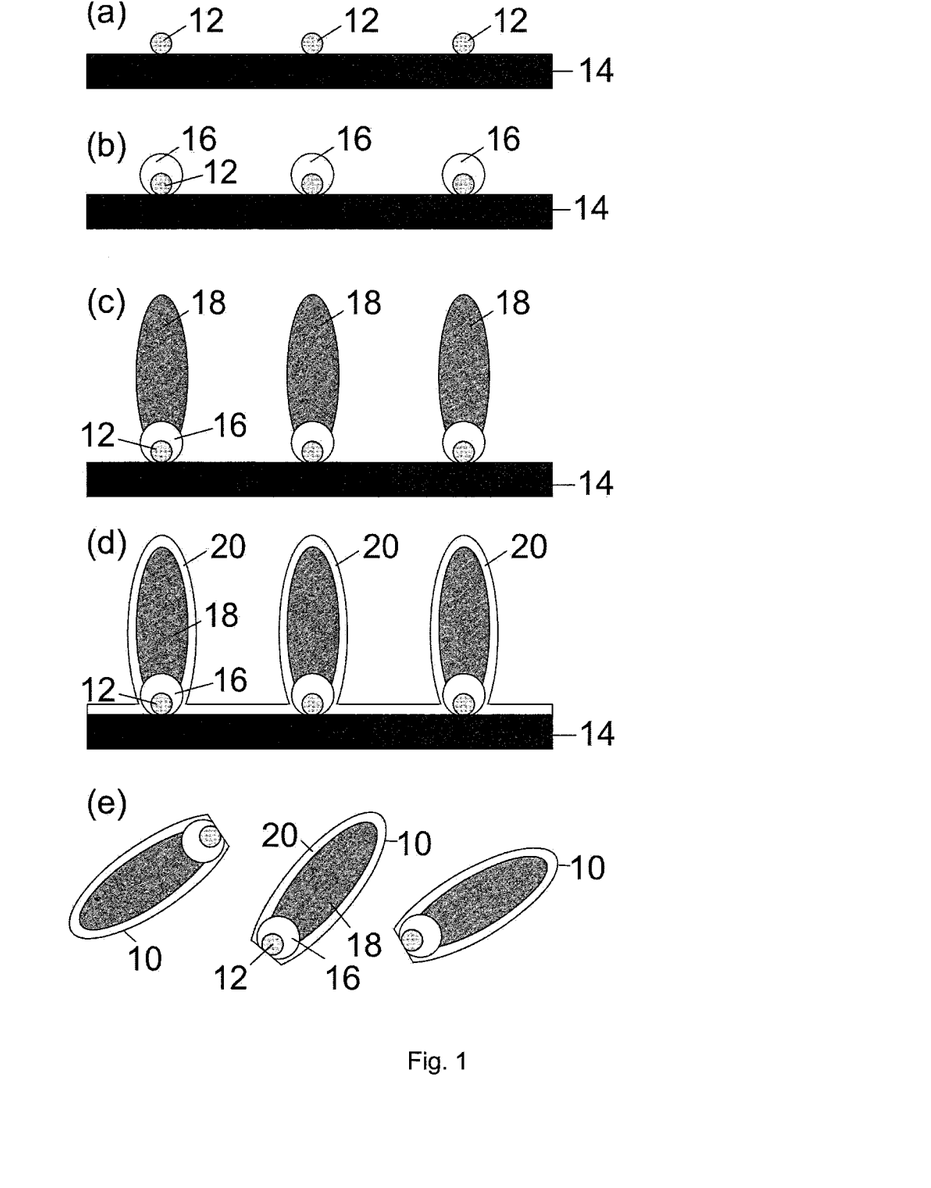
Figure 2:
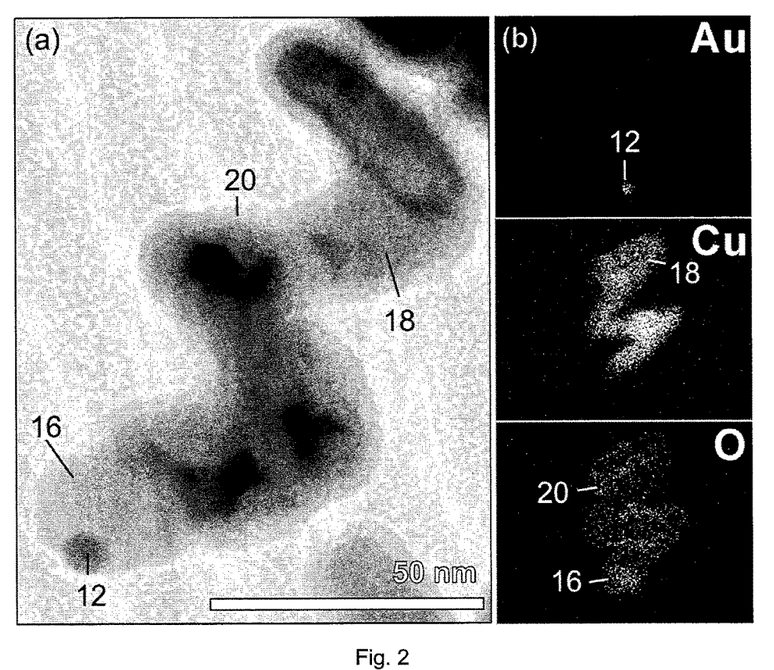

A first example of manufacture of encapsulated nanostructures will now be given with reference to the scheme of fabrication depicted in FIG. 1:

In particular FIG. 2(a) shows a TEM image of a fabricated core-shell nanohelix manufactured in accordance with the fabrication scheme discussed in relation with FIG. 1. FIG. 2b shows its corresponding EDX elemental mapping images. The different components of the core-shell particle 10 can clearly be seen. The top panel shows a small predominantly white round region which signifies the presence of Au seeds 12. The middle panel shows the helical shaped nanostructure 18 which is made of predominantly Cu. In the bottom panel, the nanostructure 18 is covered by a layer indicating the presence of O which is a combination of the shell 20 formed of $Al_2O_3$ as well as the plug 16 formed of $SiO_2$.

The images of FIG. 2b clearly show that the core 18 (Cu) was completely isolated from the outside environment surrounded by both an $Al_2O_3$ shell 20 and a $SiO_2$ plug 16. The life-time of such grown core-shell nanoparticles 10 in a highly corrosive environment (e.g. $H_2O_2$, salt containing buffer solutions, etc.) can be examined through the stability and quality of the particles by in-situ monitoring of their plasmonic, optical, electrical and/or magnetic property (see e.g. FIG. 3). This method thus enables the growth of stable nanocolloids 10 with a large selection of shapes, such as helix, zigzag, barcode, rod-shaped, etc. and a wide variety of materials of the core structure, these include but are not limited to Ag, Cu, Al, Co, Ni, Fe, Pt etc. Such a variety of structures and materials cannot be obtained with other existing techniques.

Figure 3:
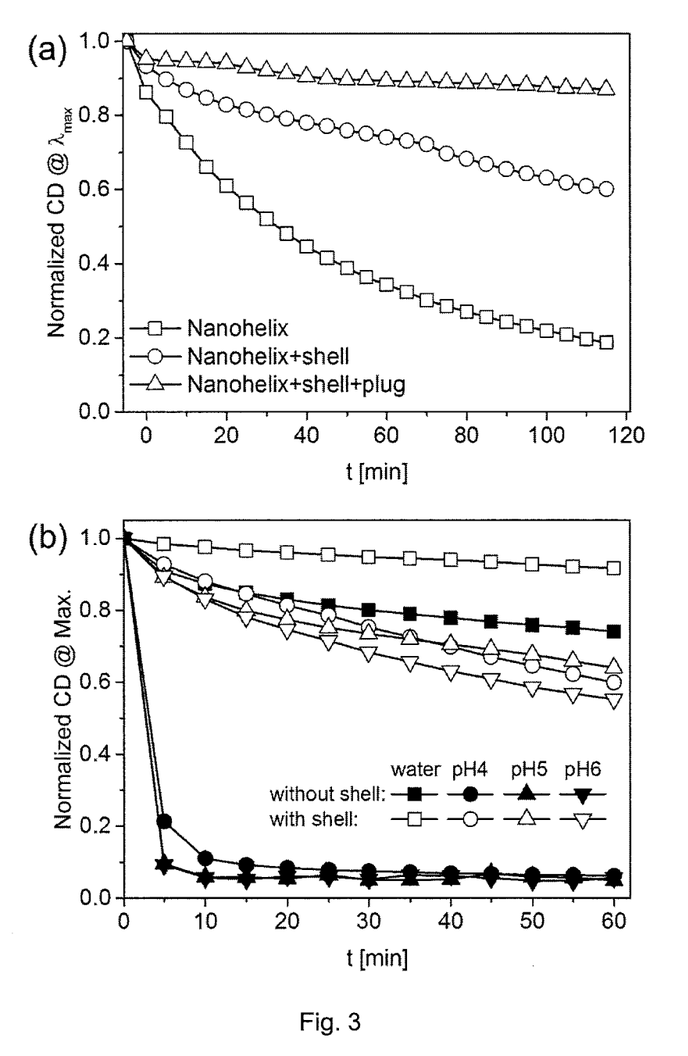

FIG. 3a shows the evaluation of the life-time of Cu nanohelix 18 (squares), Cu nanohelix 18 with $Al_2O_3$ shell 20 (circles), and Cu nanohelix 18 with $SiO_2$ plug 16 and $Al_2O_3$ shell 20 (triangles) in 1 mM $H_2O_2$ for 2 h. One can clearly see that the best protection of the Cu nanohelix 18 is achieved by completely encapsulating the Cu nanohelix 10 using a shell 20 and a plug 16. FIG. 3b shows the life-time of the Cu nanohelix 18 and Cu nanohelix 18 with $Al_2O_3$ shell 20 in the presences of acetate buffer at pH 4, 5, and 6. One can clearly see that the completely encapsulated Cu nanohelix 10 is significantly more stable than the Cu nanohelix 8.

Figure 4:
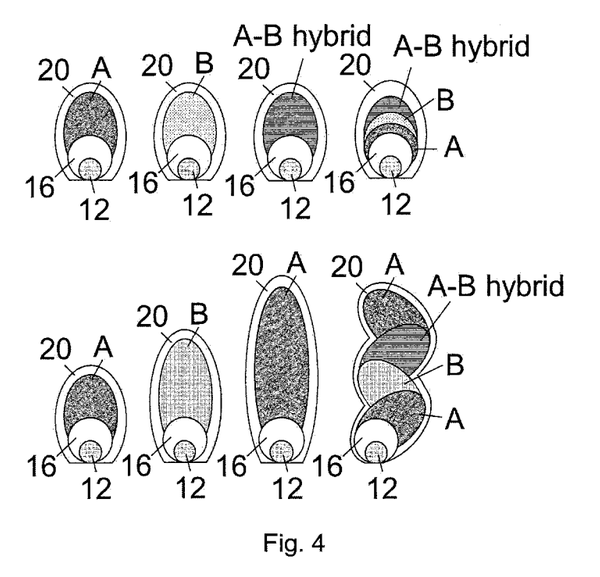
FIG. 4 examples of possible encapsulated nanostructures.

FIG. 4 shows possible examples of the core-shell particles 10. The top row shows the flexibility in the choice of material of the nanostructures 18. From left to right the core of the nanostructure 18 can either be formed of one material A or B or that the nanostructure can be composed of a hybrid of material A-B hybrid or of a multilayer structure. The lower rows show that the core-shell particles 10 can be fabricated with different geometries, such that the cores 18 have different aspect ratios, in particular the far right scheme shows the flexibility of both material and geometry.

Figure 5:
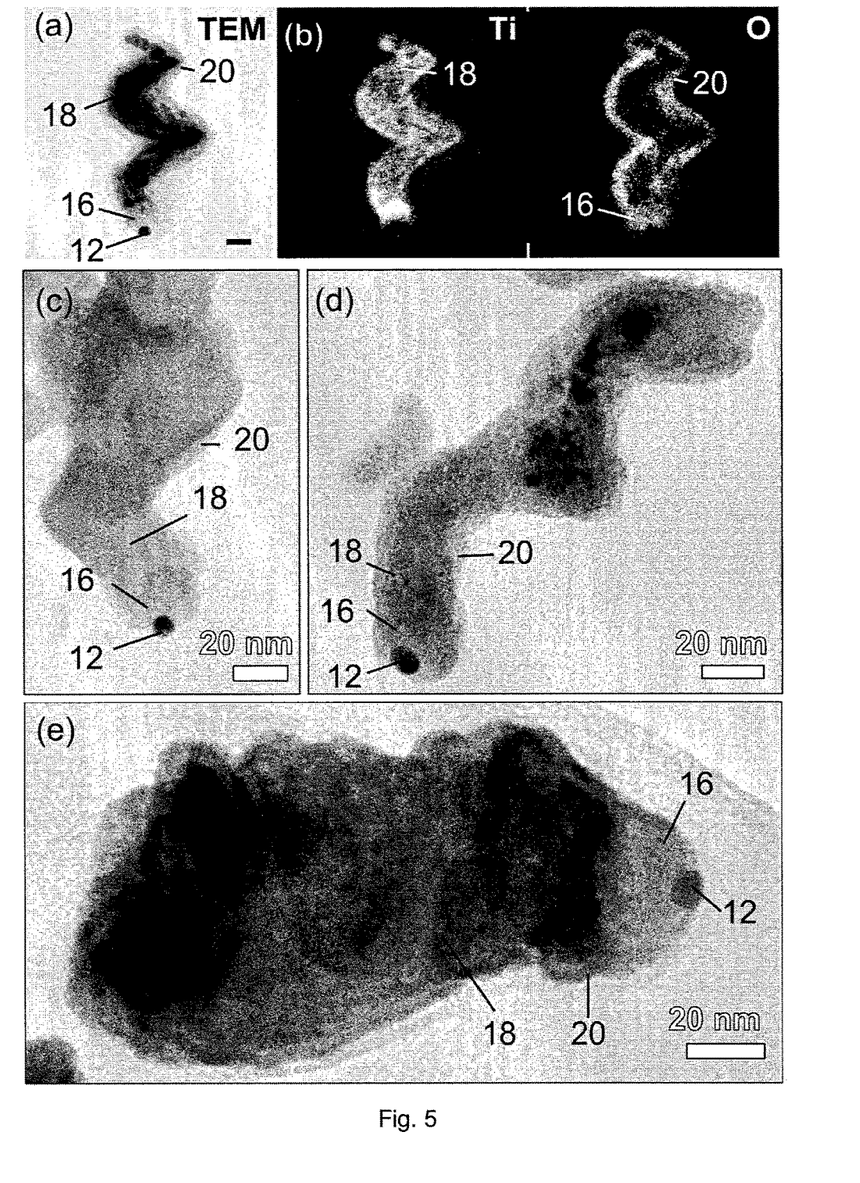
FIG. 5 TEM images of further examples of fabricated encapsulated nanostructures, a) and b) plug=$SiO_2$, core=Au-Ti, shell=a native oxide $TiO_2$, c) plug=$SiO_2$, core=Al, shell=$Al_2O_3$, and d) plug=$SiO_2$, core=Al-Fe, shell=$Al_2O_3$, e) plug=Ti, core=Co, shell=$HfO_2$, FIG. 6a-d a second scheme detailing a further fabrication process of encapsulated nanostructures, FIG. 7a-b a scheme detailing the fabrication of nanosized shells, and FIG. 8 a further scheme detailing the fabrication of coated nanostructures having a helical shape

A second example of manufacture of encapsulated nanostructures will now be given with reference to the scheme of fabrication depicted in FIG. 3: FIG. 5 shows 4 different examples of encapsulated nanostructures 10. FIG. 5(a) shows a TEM image of a fabricated core-shell nanohelix 10 manufactured in accordance with the fabrication scheme discussed in relation with FIGS. 1 and 4 respectively, but having different materials of core 18 formed of Au-Ti hybrid and shell 20 formed of $TiO_2$. FIG. 5(b) shows its corresponding EDX elemental mapping images. Left panel shows a helical shape indicating the presence of Ti which is one of the main constituents of the core 18 formed of an Au-Ti hybrid. Right panel shows an oxide layer indicating both the plug 16 formed of $SiO_2$ and the shell 20 formed of $TiO_2$. FIGS. 5(c) and (d) show TEM images of the encapsulated nanohelices having different core 18 materials of Al and Al-Fe hybrid respectively. FIG. 5(e) shows a TEM image of the encapsulated nanorod having a plug formed of Ti, core formed of Co, and shell formed of $HfO_2$.

Figure 6:
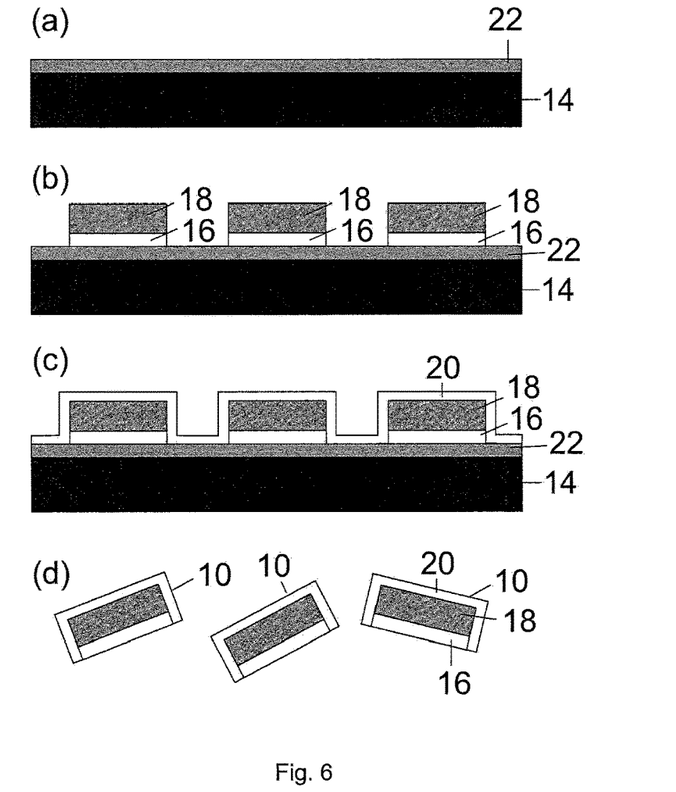

FIG. 6 shows a further scheme for the fabrication of core-shell particles 10. This scheme employs conventional lithographic techniques. In order to form the plugs 16, the substrate 14 is prepared by preparing a sacrificial layer 22 on the substrate 14 (see FIG. 6a). The sacrificial layer 22 is provided in order to easily remove the coated nanostructures 10 from the substrate 14 after the fabrication. The sacrificial layer 22 can be formed on the substrate 14 by deposition, or by spin coating or drop casting of a polymer solution. The sacrificial layer can for example be composed of salt (NaCl) or a soluble polymer and can correspondingly be removed with water or an organic solvent.

Following the fabrication of the sacrificial layer 22, the plug 16 and the core 18 are patterned on the sacrificial layer 22 (see FIG. 6b). A polymer layer is spin coated on to the sacrificial layer and it is reversely pre-patterned by using a suitable lithographic technique (e.g. photolithography, e-beam lithography, two photon lithography, nanoimprint lithography, scanning probe lithography, etc.) which consists of selective energy transfer (light expose, thermal heating, etc.) through a pre-designed mask (or template) and development of the exposed area by the commercial developer or any suitable solvent. The patterned area is then filled with the plug material 16 and the following core material 18 by a suitable growth technique (PVD, CVD, electro- or electroless-deposition, MBE, inkjet printing, etc.) thereafter the patterned polymer is removed by acetone or any appropriate solvent for its depolymerisation, or by plasma treatment (ashing, cleaning, etching, etc.).

FIG. 6c shows the formation of the shell 20 on the nanostructure 18. The shell 20 is grown by a suitable sputtering or other kind of deposition growth technique (ALD, PVD, CVD, MBE, silanization, etc.).

FIG. 6d shows the core-shell particles 10 after their removal from the substrate 14 to achieve a colloidal solution of the core-shell nanoparticles 10 by removing the sacrificial layer 22 and sonicating the particles 10 in an aqueous solution of pure water or water in stabiliser (sodium citrate, PVP, etc.). Other solutions are also possible as is the transfer to other media.

Figure 7:
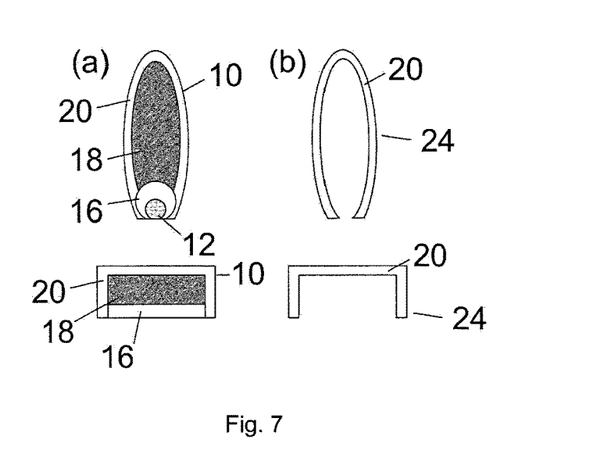

FIG. 7 shows the fabrication of colloidal shell (tube) particles 24. In particular FIG. 7(a) shows the core-shell particles 10 prior to the removal of the plug 16 and the core 18. In this respect the plug 16 and the core 18 are selected such that their respective materials can easily be dissolved or removed at the end of the shell 20 adjacent to the plug 16, e.g. when these come into contact with water or oxidizing agents. Examples of such dissolvable or removable materials are: Ag, Cu, NaCl, Co, Ga, etc.

FIG. 7b shows the remaining shell structures 20 after the sequential removal of the plug 16 and the core 18 to fabricate the shell (tube) particles 24. A dissolvable plug 16 means that the core 18 cannot be perfectly isolated from the surrounding environment, by selecting a suitable material of the core 18 , e.g. Ag, Cu, NaCl, Co, Ga, etc. this can also be readily removed by soaking it in an appropriate etchant, e.g. a mixture of ammonia and hydrogen peroxide, an acid, Piranha solution, etc. that can selectively remove the core 18 without destroying the shell 20.

Configuring the plug 16 such that it is easily dissolved or removed, also means that the core 18 can constitute e.g. a medication that can be released from the shell 20, once the plug 16 has been dissolved. In this way the shell 18 could be a container for medication. Thus, choosing a plug 16 that is dissolved in a suitable environment, possibly triggered by a biological marker, can facilitate the triggered release of a material of the core 18 that may have desirable properties, e.g. the material can be used for the targeted delivery of a compound or as an imaging marker at a location of application.

In the same way applications exist in which the shell 20 encapsulates a super-paramagnetic material of any shape, preferably of a rod-shaped form. After coating the super-paramagnetic nanostructure 18 with an oxide, silane chemistry can be used to chemically functionalize this coated nanostructure 10. The chemical functionalization may be selected such that it targets specific cell types and/or facilitates endocytosis of the particles. Thereafter it is available for applications of low frequency magnetic fields that can be used to kill or disable the cells or to induce other cell functions following the mechanical stimulation. The super-paramagnetic nanostructure 18 can be tracked and/or guided as it is moved so that the targeted specific cell types and/or the particles in question can be reached by the super-paramagnetic nanostructure 18.

Figure 8:
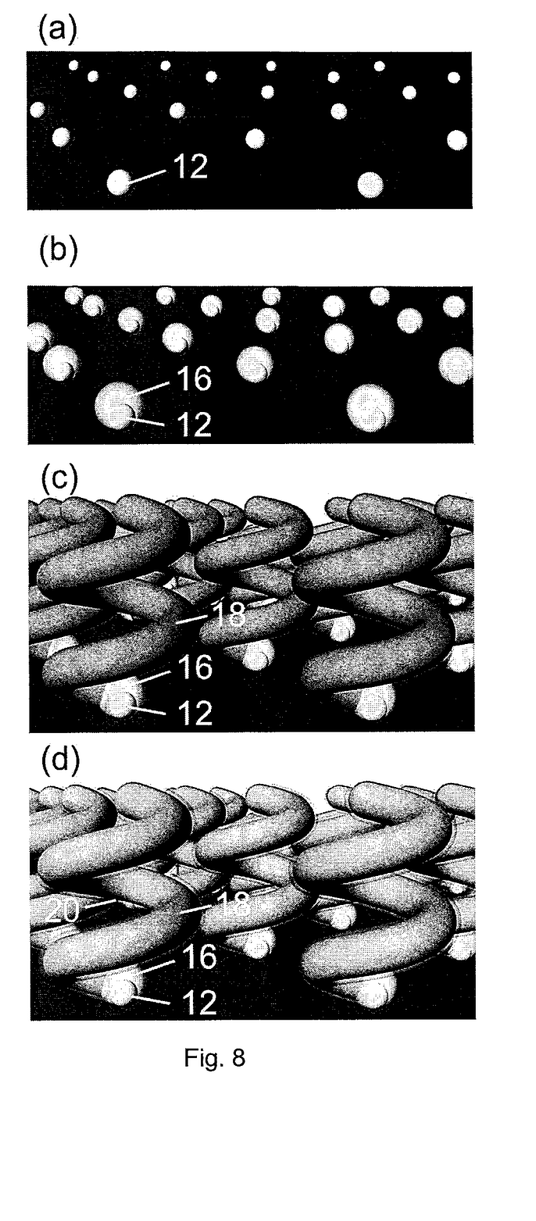

A detailed example of manufacture will be explained according to the scheme depicted and explained with reference to FIG. 8. The core-shell particles 10 having helical shape were produced by a so-called shadow deposition technique (see FIG. 1). The obtained core-shell particles 10 can be manipulated with regard to their material shape and composition.

In a first step, an array of the Au nanoseeds 12 was patterned on a substrate 14 by block-copolymer micelle nanolithography (BCML) (see the top illustration of FIG. 8a). In order to produce the seeds 12 on the substrate 14 Poly (styrene)-b-poly (2-vinylpyridine) (S units: 1056; VP units: 671) was dissolved in toluene at a concentration of 4 mg·mL$^{-1}$ and stirred overnight. Subsequently HAuCl$_4$.3 (H$_2$O) was added to the polymer solution at a molar ratio of 0.5 per vinyl pyridine unit and stirred for at least 48 hrs. This generated self-assembled spherical micelles loaded with Au salts in their cores. In order to form a quasi-hexagonally close-packed array of the micelles, the micelles were spin-coated on a Si (or glass) wafer at 8,000 rpm for 1 min. Following this the micelles were removed using a 10% H$_2$ and 90% Ar plasma treatment (power: 350 W, pressure: 0.4 mbar, time: 45 min). Thereby Au was reduced and crystallised as seeds 12 of nanoparticle size having 12 nm in diameter and gaps of approximately 100 nm between adjacent seeds 12.

Examples of wafers that can be used are: glass (SiO$_2$, sapphire, ITO, etc.), Si, Ge, silicon on insulator (SOI), silicon nitride, and gallium arsenide etc.

Although Au nanoparticles were arranged on the substrate 14 as seeds 12 in this example, naturally also other materials, such as Pt, Ag, In, Fe, Zr, Al, Co, Ni, Ga, Sn, Zn, Ti, Si, Ge, Fe, or thereof alloys can be deposited as seeds 12. Also the sizes of the seeds 12 can be varied, for example for a size range of 2 to 30 nm. Moreover, the gaps present between the seeds 12 can be varied for size ranges of, for example, 20 to 300 nm. The size of the seeds 12 and the spacing between the seeds 12 and the pattern of the seeds 12 can readily be tuned by controlling the concentration and composition of the metal ions and the block-copolymers. Moreover, any lithographic technique (see e.g. FIG. 4) that can fabricate the array of the structures at the nanoscale to microscale can be used rather than BCML. In a second step the array of nano-seeds 12 was exposed to a SiO$_2$ vapour flux in a physical vapour deposition (PVD) system at an incident angle of α=83 to 87° to grow plugs 16 on the nanoseeds 12 using glancing angle deposition (GLAD). In order to grow the plugs 16, the GLAD system has two electron-beam evaporators that permit the growth of pure, alloyed (or hybrid), and multi-layered nanostructures with a base pressure of approximately 1×10$^{-6}$ mbar or lower. The substrate manipulator provides independent control over the azimuthal direction φ, and molecular flux direction a during deposition. To grow plugs 16, the flux angle α and the azimuthal rotation rates per unit thickness dφ/dθ were maintained at 85° and 18±0.1° /nm with closed-loop feedback based on measurements of material deposition rates on a quartz crystal monitor (QCM). The alloy stoichiometry can be controlled by measuring and controlling the deposition rates on the QCMs from each evaporator independently.

Using two electron-beam evaporators, and two degrees-of-freedom (DOF) of rotation of the substrate during the growth process, 3D cores of nanostructures including spheres, rods, helices, zigzags, etc. can readily be attained. The growth of helices is for example detailed in the publication by A. G. Mark, J. G. Gibbs, T. -C. Lee, P.Fischer: "Hybrid nanocolloids with programmed 3D-shape and material composition", Nature Materials 12, 802 (2013).

In a subsequent step a thin alumina ($Al_2O_3$) layer was grown to cover the entire surface of the substrate as a shell 20 using atomic layer deposition (ALD) at T=100° C. with 0.1 nm/cycle of the growth rate by injecting trimethylaluminum (TMA) and deionized $H_2O$ repeatedly.

This process is not limited to ALD, so that any growth technique that permits the growth of very thin uniform layers on the entire surface of the core 18 can alternatively be used to form a shell 20. Such processes include sputtering, PVD, MBE, CVD, silanization (gas or solvent phase), etc. Moreover, the GLAD technique can be directly used for the growth of the shell 20 by manipulating the substrate during the growth.

In order to detach the coated nanostructures 10 from the substrate 14 these were separated by sonicating a piece of sample wafer (~1 $cm^2$) in an aqueous solution of 1 mM sodium citrate (or other appropriate stabilizers) for ~2 min.

The method described in the foregoing allows the growth of custom tailored nano-particles 10 that for instance are magnetic and that can be used in biological environments, e.g. bood, cells, etc. The shell permits chemical functionalization and the core structure can give the nanoparticle functions that cannot or only with difficulty be realized with other methods; it is possible to grow particles that contain multiple functionalities and that are stable in solution by use of the method described herein:

1. MRI contrast agent: Gd, Fe oxides ($Fe_2O_3$, $Fe_3O_4$, etc.), FePt, and Mn are commonly used as a contrast agent to improve the visibility of internal body structures in magnetic resonance imaging (MRI). The method can permit the fabrication of image contrast agents with not only such materials in a way to improve their lifetime and decrease their toxicity, but also using materials with magnetic properties for strong signal contrast. Such a new class of colloidal particles expands their utility as an imaging contrast agent for various imaging techniques, for instance magnetic resonance imaging (MRI), magneto-motive ultrasound imaging, photoacoustic imaging, surface enhanced Raman spectroscopy (SERS) imaging, dark-field imaging, etc.
2. Micro- /Nano- robots: Helical shaped structures are used as swimmers and propellers in solution and biological media. The 'plug+shell' concept described herein enables the surface chemistry on the plug 16 and the shell 20 to be selected for drug delivery (by molecular binding), for local surgery, and for dynamic spectroscopy and imaging (by Brownian motion or modulation) as well as protecting all the sections of the propellers (see e.g. FIG. 6*a*) to expand their use in harsh or biological environments. The plug and shell can at the same time encapsulate and thus chemically and physically isolate a magnetic material that is cytotoxic.
3. Hyperthermia therapy (a form of medical therapy): wireless heating phenomena including magnetic induction heating and plasmonic heating is a therapeutic procedure that can be used for hyperthermia therapy. Hence, the core-shell nanoparticles 10 with a magnetic core, a plasmonic core, or an alloy or composite of materials that facilitate can be used for medical therapy. The particles 18 have a protective shell 20 that prevents the particle 18 from the environment and the environment from the material. Another form of medical therapy utilizes the torque and/or force that can be exerted on the magnetic particle to kill or to mechanically stimulate cells. For this the particles 18 are preferentially shape anisotropic, including rod-shaped, and consist of a magnetic material that is paramagnetic, superparamagnetic, or ferromagnetic such that a magnetic field can be used to exert a torque on the particles 18. The magnetic material may be grown in a form that is favourable for the magnetic application. The shell material 20 and the plug material 16 isolates the particle form the environment and at the same time offers the possibility of chemical functionalization and/or binding with molecules.
4. Diagnostic probe: Encasing a material in a nanostructure to be used as a diagnostic probe, including as magnetic (or magneto-plasmonic) particles to analyse the rheology (e.g. the viscosity or viscoelasticity) of a medium or a fluid, e.g. blood. On the other hand, the metallic nanoparticles can be used for early diagnosis of diseases by monitoring the change of the effective refractive index on the surface of the particles via localised surface plasmon resonance (LSPR). The protective shell 20 renders them stable and prevents the particle-particle contact which would affect the spectrum. Using the well-known molecular binging schemes (ELISA, antibody-antigen interaction, biotin-avidin affinity, etc.) on the plasmonic particles enables selective target detection as well as multiplexing. Such particles can also be used for SERS for both in-vitro and in-vivo multiplexing.
5. Targeted treatment: Using a plug 16 that is responsive to a medium can be used to have the plug 16 specifically removed or corroded in the vicinity or upon contact with the medium, or tissue of interest. This can then open the structure and permit the release of the encased core 18 that has a specific use of function. Alternately a radioactive material can also be enclosed in a shell 20.
6. Metamaterials: the method permits the fabrication of stable metamaterials in solution, namely metacolloids, metafluids, etc. This scheme is potentially interesting for fundamental science as well as device applications.
7. Energy generation and storage: Structuring of metal oxides, semiconductors, and plasmonic materials with proper design for transferring electron carriers allow photocatalytic devices with the flexibility of the reacting wave-length range for energy generation from nature. On the other hand, the yolk-shell structure having a void space between the core and the shell is useful for Li-ion battery applications since this geometry provides high stability during the lithiation process involving the volume expansion of the core part. Hence, fabricating such geometry using our method enables large selectivity of materials as well as shapes.
8. Colloid science: Use of corrosive, oxidised, volatile, soluble, explosive, toxic, liquid, and/or reactive materials in solution that cannot be used to make nanoparticles by conventional means and to protect these materials.

Prior art relied known to the inventors and from which this application is distinguished:

1. Li, J. F.; Huang, Y. F.; Ding, Y.; Yang, Z. L.; Li, S. B.; Zhou, X. S.; Fan, F. R.; Zhang, W.; Zhou, Z. Y.; WuDe, Y.; Ren, B.; Wang, Z. L.; Tian, Z. Q., Shell-isolated nanoparticle-enhanced Raman spectroscopy. *Nature* 2010, 464 (7287), 392-395.
2. Li, J. F.; Tian, X. D.; Li, S. B.; Anema, J. R.; Yang, Z. L.; Ding, Y.; Wu, Y. F.; Zeng, Y. M.; Chen, Q. Z.; Ren, B.; Wang, Z. L.; Tian, Z. Q., Surface analysis using shell-isolated nanoparticle-enhanced Raman spectroscopy. *Nat. Protocols* 2013, 8 (1), 52-65.

3. Reineck, P.; Gómez, D.; Ng, S. H.; Karg, M.; Bell, T.; Mulvaney, P.; Bach, U., Distance and Wavelength Dependent Quenching of Molecular Fluorescence by Au@SiO2 Core-Shell Nanoparticles. ACS *Nano* 2013, 7 (8), 6636-6648.
4. Wang, W.; Li, Z.; Gu, B.; Zhang, Z.; Xu, H., Ag@SiO2 Core-Shell Nanoparticles for Probing Spatial Distribution of Electromagnetic Field Enhancement via Surface-Enhanced Raman Scattering. *ACS Nano* 2009, 3 (11), 3493-3496.
5. Song, C.; Chen, J.; Abell, J. L.; Cui, Y.; Zhao, Y., Ag—SiO2 Core-Shell Nanorod Arrays: Morphological, Optical, SERS, and Wetting Properties. *Langmuir* 2011, 28 (2), 1488-1495.
6. Hu, Z.; Liu, Z.; Li, L.; Quan, B.; Li, Y.; Li, J.; Gu, C., Wafer-Scale Double-Layer Stacked Au/Al2O3@Au Nanosphere Structure with Tunable Nanospacing for Surface-Enhanced Raman Scattering. *Small* 2014, 10 (19), 3933-3942.
7. Gao , C.; Lu , Z.; Liu , Y.; Zhang, Q.; Chi, M.; Cheng, Q.; Yin, Y., Highly Stable Silver Nanoplates for Surface Plasmon Resonance Biosensing. *Angewandte Chemie International Edition* 2012, 51 (23), 5629-5633.
8. Yang, X. H.; Fu, H. T.; Wong, K.; Jiang, X. C.; Yu, A. B., Hybrid Ag@TiO 2 core-shell nanostructures with highly enhanced photocatalytic performance. *Nanotechnology* 2013, 24 (41), 415601
9. A. G. Mark, J. G. Gibbs, T.-C. Lee, P.Fischer: "Hybrid nanocolloids with programmed 3D-shape and material composition", Nature Materials 12, 802 (2013)
10. P. Fischer and A. Ghosh, Magnetic nanostructured propellers, U.S. Pat. No. 8,768,501
11. K. J. Robbie, M. J. Brett, Glancing angle depositions if thin films, U.S. Pat. No. 6,206,065
12. M. Arnold, T. Lohmüller, J. Spatz, Verfahren zur Herstellung von flächigen
    Größen- oder Abstandsvariationen in Mustern von Nanostrukturen auf
    Oberflächen, DE102007017032B4.

LIST OF REFERENCE NUMERALS 10 encapsulated nanostructure/core-shell particle
12 seeds
14 substrate
16 plug
18 nanostructure/core
20 shell
22 sacrificial layer
24 shell tube particles
A, B type of material

The invention claimed is:

1. A method for encapsulating a nanostructure, the method comprising the steps of:
   providing a substrate;
   forming a plug composed of plug material at said substrate;
   forming a nanostructure at said plug;
   forming a shell composed of at least one shell material on external surfaces of the nanostructure, with the at least one shell material covering said nanostructure and at least some of the plug material, whereby the shell and the plug encapsulate the nanostructure, wherein the nanostructure is formed by a growth technique selected from the group of members consisting of physical vapour deposition, chemical vapour deposition, electro- or electroless deposition, molecular beam epitaxy and inkjet printing, and wherein the nanostructure is fabricated using a material that can be deposited or grown as a nanostructure on top of a seed wherein a step of providing seeds on the substrate prior to or directly after the step of forming a plug is provided, with the seeds being provided in a patterned manner on said substrate or on the plug.

2. The method in accordance with claim 1, wherein the plug is formed by a sputtering or other deposition processor by a printing or nanoimprinting method.

3. The method in accordance with claim 1, wherein the shell is formed by a sputtering or other deposition process or by a printing or nanoimprinting method.

4. The method in accordance with claim 1, wherein a material of the plug is selected from the group of materials comprising: oxides, or inert stable materials including metals or metal alloys.

5. The method in accordance with claim 1, wherein a material of the shell is selected from the group of materials comprising: oxides, inert stable materials including metals or metal alloys.

6. The method in accordance with claim 1, wherein the shell is formed from the same material as the plug.

7. The method in accordance with claim 1, wherein at least one of the plug and the shell is adapted to act as a physical and/or a chemical barrier from the substrate and/or the environment.

8. The method in accordance with claim 1, wherein the nanostructure is formed at said plug having a size selected in the range of 10 nm to 10000 nm in at least one dimension thereof.

9. The method in accordance with claim 1, wherein the nanostructure is composed of at least one core material.

10. The method in accordance with claim 9, wherein, in the case of plural materials, these different materials are either mixed or arranged adjacent to one another.

11. The method in accordance with claim 1, wherein a material of the nanostructure is selected from the group of materials consisting of: Ag, Au, Cu, Al, Co, Ni, Fe, Gd, Pt, Mg, Ca, Na, Li alloys, oxides, a Cu-nanohelix, a contrast agent for imaging, magnetic material for hyperthermia treatment, nanopropeller shapes for movement and drug delivery, magnetic materials for magnetic therapy, radioactive materials, materials exhibiting plasmonic activity, materials susceptible to oxidation and combinations of the aforementioned materials.

12. The method in accordance with claim 1, comprising the further step of separating the encapsulated nanostructure from the substrate to form a discrete encapsulated nanostructure.

13. The method in accordance with claim 1, further comprising the step of removing the plug and the nanostructure to form a hollow shell.

14. The method in accordance with claim 1, comprising the further step of providing a sacrificial layer on the substrate prior to the step of forming the plug.

15. The method in accordance with claim 1, wherein the step of forming the plug and/or the step of providing the nanostructure is effected by a lithographic technique.

16. The method in accordance with claim 1, wherein the shell is composed of a plurality of different materials or shell layers of different material.

17. The method in accordance with claim 1, wherein the shell is deposited in the form of at least one layer of a biologically active or pharmaceutical material and at least one further layer encapsulating the at least one layer of biologically active or pharmaceutical material.

* * * * *